United States Patent
Vig et al.

(10) Patent No.: US 6,247,354 B1
(45) Date of Patent: Jun. 19, 2001

(54) TECHNIQUES FOR SENSING THE PROPERTIES OF FLUIDS WITH RESONATORS

(75) Inventors: John R. Vig, Colts Neck; Arthur Ballato, Oceanport, both of NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/531,630

(22) Filed: Mar. 21, 2000

Related U.S. Application Data

(63) Continuation-in-part of application No. 09/078,053, filed on May 13, 1998, now abandoned.

(51) Int. Cl.$^7$ ................................................. G01N 11/10
(52) U.S. Cl. .......................... 73/54.41; 73/32 A; 73/579
(58) Field of Search .............................. 73/24.06, 54.41, 73/580, 579, 64.53, 24.05, 32 A

(56) References Cited

U.S. PATENT DOCUMENTS

| | | |
|---|---|---|
| 2,212,139 | 8/1940 | Baldwin et al. . |
| 2,743,144 | 4/1956 | Bottom et al. . |
| 5,201,215 * | 4/1993 | Granstaff et al. ................... 73/54.41 |
| 5,416,448 | 5/1995 | Wessendorf . |
| 5,705,399 * | 1/1998 | Larue ................................... 436/501 |
| 5,852,229 * | 12/1998 | Josse et al. ......................... 73/24.06 |
| 5,869,763 * | 2/1999 | Vig et al. ............................. 73/580 |
| 5,936,150 * | 8/1999 | Kobrin et al. ...................... 73/24.06 |
| 6,009,589 * | 12/1999 | Rodahl et al. ...................... 73/54.41 |
| 6,029,500 * | 2/2000 | Tom .................................... 73/31.05 |

OTHER PUBLICATIONS

Hammond et al, An Acoustic Automotive Engine Oil Quality Sensor, Proceedings of the 1997 IEEE International Frequency Control Symposium, IEEE Catalog No. 97CH36016, pp. 72–80, May 28–30 1997.

Zhang et al., "Contribution of Amplitude Measurement in QCM Sensors", IEEE Transactions on Ultrasonics, Ferroelectrics, and Frequency Control, vol. 43, No. 5, pp. 942–947, Sep. 1996.

Martin et al., "Measuring Liquid Properties with Smooth– and Textured–Surface Resonators", 1993 IEEE International Frequency Control Symposium, IEEE Catalog No. 0–7803–0905–7/93, pp. 603–608, 1993.

* cited by examiner

Primary Examiner—Hezron Williams
Assistant Examiner—C. D. Garber
(74) Attorney, Agent, or Firm—Michael Zelenke; George B. Tereschuk

(57) ABSTRACT

A technique of determining the properties of a liquid. One or more resonators are exposed to air or another reference fluid of known properties. Oscillator circuits drive the resonators at at least two different frequencies. Frequency counters measure the fluid-operating frequencies of the resonators while they are in contact with the reference fluid. The resonators are then immersed in liquid as the oscillator circuits drive the resonators. The liquid-operating frequencies are measured by the frequency counters while the resonators are in contact with the liquid. A computer compares the fluid-operating frequencies and the liquid-operating frequencies to obtain difference frequencies that are independent functions of the liquid's properties. A computer determines the liquid properties from the difference frequencies.

47 Claims, 4 Drawing Sheets

TECHNIQUES FOR SENSING THE PROPERTIES OF FLUIDS WITH RESONATORS

CONTINUATION-IN-PART

This application is a Continuation-In-Part of U.S. Patent And Trademark Office application Ser. No. 09/078,053, entitled, "Techniques For Sensing The Properties Of Fluids With Resonators," designated as which was filed on May 13, 1998, by the same inventors herein, and is about to be abandoned. This Continuation-In-Part is being filed under 35 USC §120 and 37 CFR §1.53, and priority from that application is hereby claimed.

GOVERNMENT INTEREST

The invention described herein may be manufactured, used, sold, imported and licensed by or for the Government of the United States of America without the payment to us of any royalty thereon.

FIELD OF THE INVENTION

This invention relates generally to the field of measuring and testing fluids. More particularly it relates to techniques of using crystal resonators as sensors for sensing fluid properties.

BACKGROUND OF THE INVENTION

Sensing a mass deposited onto a surface of a piezoelectric resonator is a technique that has been used in the measuring and testing field for decades. A conventional quartz crystal microbalance (QCM) typically includes a piezoelectric resonator capable of sensing loads less than a microgram. For small amounts of mass, a change in the frequency of a piezoelectric resonator is proportional to a mass change. Thus, QCM's have been used in a variety of applications, such as detectors for measuring humidity or the presence of other adsorbed gases, and as sensors for monitoring film thickness in thin-film deposition processes, to name just a few.

In the past, QCM sensors were generally designed to operate in air or other gaseous environments. More recently, QCM sensors have been designed to operate in liquids. For instance, the following article describes a specific application of an acoustic sensor having a quartz crystal resonator that is designed to operate in oil: Hammond et al., AN ACOUSTIC AUTOMOTIVE ENGINE OIL QUALITY SENSOR, Proceedings of the 1997 IEEE International Frequency Control Symposium, IEEE Catalog No. 97CH36016, pp. 72–80, 28–30 May 1997.

The Hammond et al. article notes that the viscosity of oil in an automobile is perhaps the single most important technical parameter of a modern crankcase lubricant. Thus, Hammond et al. propose an onboard sensor for measuring viscosity changes of crankcase oil in an automobile or other similar mechanisms. They describe a technique of measuring the viscosity of oil by operating an AT-cut quartz resonator immersed in the oil The sensor includes a drive circuit that excites a shear mechanical motion in the resonator, which motion is transferred to the oil. The oil essentially acts as a mechanical load to the quartz resonator and this mechanical load does influence the quality factor (Q) and other electrical properties of the resonator. The Hammond et al. article describes how a change in the electromechanical quality factor Q of a resonator is proportional to the mass accumulation at the resonator-oil interface. As such, changes in the resonant frequency and the amplitude of the resonance signal, due to the mechanical loading, are found to be proportional to the product of the density and viscosity of the oil. Thus, the combined effects of phase and amplitude changes of a sensing signal may be measured to monitor changes in the oil viscosity.

Others have used similar techniques to measure the properties of a variety of different liquids. The following articles describe resonator sensors capable of making simultaneous measurements of liquid density and viscosity: Zhang et al., CONTRIBUTIONS OF AMPLITUDE MEASUREMENT IN QCM SENSORS, IEEE Transactions on Ultrasonics, Ferroelectrics, and Frequency Control, Vol. 43, No. 5, pp. 942–947, September 1996; and Martin et al., MEASURING LIQUID PROPERTIES WITH SMOOTH- AND TEXTURED-SURFACE RESONATORS, 1993 IEEE International Frequency Control Symposium, IEEE Catalog No. 0-7803-0905-7/93, pp. 603–608, 1993.

The Zhang et al. article describes how a QCM, having an AT-cut quartz resonator, can detect changes in viscosity and density of a liquid. This article indicates that when a QCM operates in a liquid, the total frequency change consists of two effects, one due to mass loading and the other due to "liquid damping." Further, according to Zhang et al., one cannot distinguish the mass loading effect from the total frequency change by only frequency measurement. Thus, a standard technique of using a QCM in liquids is to simultaneously measure changes in a frequency and a quality factor Q (or changes in equivalent circuit parameters). This allows separation of the mass loading effect from the liquid damping effect.

The Martin et al. article describes an improved method that uses a dual-resonator sensor with two AT-cut quartz resonators, one with a smooth surface and the other with a textured or rough surface. The surface texture comprises ridges, which are oriented perpendicular to the direction of surface shear displacement, i.e., the X crystalline direction. When operated in a liquid, the smooth resonator generates plane-parallel laminar flow in the adjacent liquid, which causes a resonator frequency shift that is a function of liquid density and viscosity. A textured resonator, however, traps a quantity of liquid in excess of that entrained by a smooth surface. The trapped liquid behaves as an ideal mass layer, causing an additional frequency shift that depends only on density and not viscosity.

In the Martin et al. sensor, each resonator is driven by an independent oscillator circuit that provides the following two outputs: a radio frequency (RF) signal that tracks resonant frequency and a direct current (DC) voltage proportional to motional resistance. Baseline responses are determined by measuring resonant frequency and motional resistance for each resonator before their immersion in a liquid. Changes in resonator responses are then measured separately for the smooth and textured resonators after immersion. A computer connected to the sensor calculates density and viscosity. In particular, the liquid density is first calculated from the difference in responses measured between the smooth and textured devices. Having determined liquid density, the response of the smooth resonator is then used to calculate liquid viscosity. Thus, the Martin et al. method measures a frequency change and a quality factor (Q) change (or a change in equivalent circuit parameters) for each resonator separately.

Although standard techniques of sensing the properties of fluids have served the purpose, they have not proved entirely satisfactory when making highly sensitive measurements of fluid properties, including viscosity and density. Sensor designers acknowledge that while changes in frequency can be measured with great accuracy, changes in Q, motional resistance or any other quantity are normally measured with significantly less accuracy. Q measurements for high-Q devices are typically made with accuracies of two to four significant figures, whereas the frequencies of stable frequency sources can be measured with accuracies of 14 significant figures. For lower Q devices, such as resonators immersed in a fluid, both the Q and frequency measurement accuracies are lower, however, the frequency measurement accuracies are still orders of magnitude higher than the Q measurement accuracies.

Sensor fabricators have also recognized problems with using resonators with smooth and textured surfaces. Changes in frequency and Q depend not only on a liquid's properties, but also on a resonator's surface roughness. However, it is difficult to produce surfaces of identical surface roughness, i.e., it is difficult to produce a standard rough surface. An additional difficulty with the prior art is that temperature can greatly affect the properties of fluids, e.g., the fluid's viscosity. It is well known that, for example, the viscosity of many oils and lubricants vary with temperature, and also with degradations due to chemical changes. Measuring frequency and Q changes alone cannot determine the temperature of the fluid simultaneously with the fluid's viscosity and density. Therefore, when only frequency and Q are measured and a viscosity change is detected, it is not possible to determine the cause of the viscosity change; it could be due to a temperature change or to a change in the quality of the fluid, or to a combination of factors.

SUMMARY OF THE INVENTION

The general purpose of this invention is to provide Techniques for sensing the properties of fluids by means of frequency measurements alone. To attain this, the present invention contemplates fluid sensors that employ one or more resonators driven at a multiplicity of frequencies. The properties of a liquid contacting these resonators are determined by measuring a multiplicity of frequency changes, which essentially resolve various causes of these frequency changes, such as mass loading, liquid density, liquid viscosity and temperature. Also, the present techniques involve the use of resonators that employ easily reproducible crystals, as for example polished crystals, or lapped and etched crystals. The crystals can be manufactured at low cost because the tolerances on the crystals' angles of cut and frequencies are very loose. The absolute frequencies are unimportant; information is derived from the measured changes in the frequencies of resonators.

According to one aspect of the invention, a sensor for determining the properties of a liquid includes one or more resonators having liquid-contacting surfaces. An oscillator circuit drives the resonators at one or more different frequencies. A frequency counter connected to the oscillator measures the operating frequencies of the resonators before and after the surfaces are in contact with the liquid. A computer that is responsive to the frequency counter includes a liquid property system for determining difference frequencies by comparing the operating frequencies measured by the frequency counter with predetermined reference frequencies. The computer determines the properties of the liquid from the difference frequencies.

Another aspect of the invention includes a method of determining the properties of a liquid having the following steps: providing a plurality of piezoelectric resonators each with a fluid-contacting surface; exposing the fluid-contacting surfaces to a reference fluid having known properties; driving the resonators at one or more different frequencies; measuring the fluid-operating frequencies of the resonators while the surfaces are in contact with the reference fluid; exposing the fluid-contacting surfaces to the liquid measurand; driving the resonators and driving one resonator simultaneously at the plurality of different frequencies; measuring the liquid-operating frequencies of the resonators while the surfaces are in contact with the liquid measurand; determining difference frequencies by comparing the reference-fluid-operating frequencies with corresponding ones of the liquid-measurand-operating frequencies; and determining the properties of the liquid measurand from the said difference frequencies.

The exact nature of this invention, as well as other objects and advantages thereof, will be readily apparent from consideration of the following specification relating to the annexed drawings.

DETAILED DESCRIPTION OF THE PREFERRED EMBODIMENTS

Figure 1:
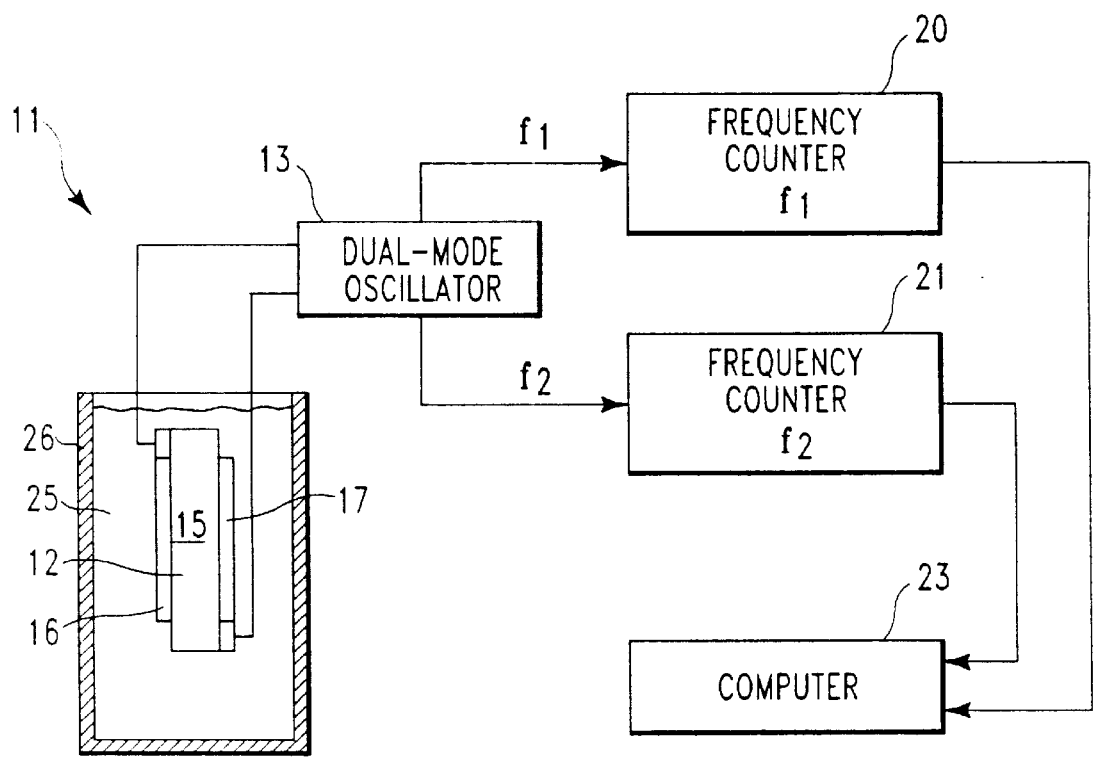
FIG. 1 is a schematic diagram of a sensor system with a piezoelectric resonator immersed in a liquid in accordance with the present invention.
Figure 2:
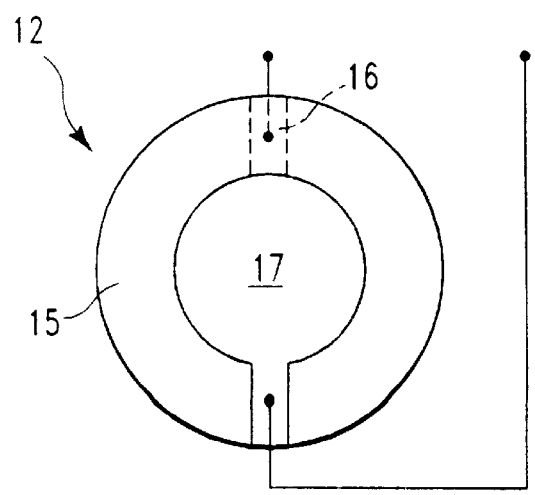
FIG. 2 shows a front view of the piezoelectric resonator shown in FIG. 1.

Referring now to the drawings, FIGS. 1 and 2 show sensor system 11 having piezoelectric resonator 12 driven by dual-mode oscillator 13 for operation at frequencies $f_1$ and $f_2$. Resonator 12 includes piezoelectric plate 15 with metallic electrodes 16 and 17 deposited on opposite major surfaces thereof. Plate 15, which has a circular cross section as seen in FIG. 2, is sliced from a piezoelectric crystal, such as quartz. Resonator 12 is immersed in non-conductive liquid 25 located in container 26. Oscillator 13 provides two outputs, an $f_1$ output and an $f_2$ output, that respectively connect to frequency counters 20 and 21. The outputs of frequency counters 20 and 21 connect to computer 23.

Oscillator circuits capable of driving resonator 12 are well known in the art. For instance, U.S. Pat. No. 5,416,448, which issued on May 16, 1995 to Otto Wessendorf, discloses oscillator circuits of the type that may be used to implement oscillator 13. In particular, the Wessendorf patent describes a Lever oscillator for use in high resistance resonator applications. Thus, the Lever oscillator would be particularly effective for driving resonator 12 when operating in mediums such as liquid 25. Other conventional instruments, such as network analyzers or reflectometers, may also be used for driving resonator 12.

Figure 3:
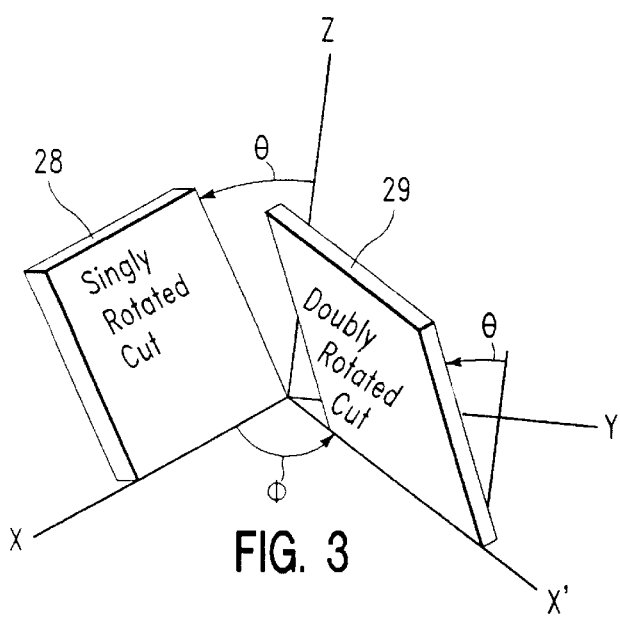
FIG. 3 is a schematic pictorial view showing slicing planes for singly rotated and doubly rotated cuts with respect to the conventional orthogonal crystallographic X-Y-Z axes, and rotation angles $\theta$ and $\phi$.

FIG. 3 shows conventional X-Y-Z crystallographic axes with slicing planes 28 and 29 located thereon. Plane 28 represents a plane along which a singly rotated cut would be made in a crystal with respect to its X-Y-Z axes. Plane 29 illustrates the plane along which a doubly rotated cut would be made. In particular, a singly rotated cut is made along a plane that includes the X-axis, and wherein the Z-axis forms an angle $\theta$ with respect to that plane. A doubly rotated cut is made along a plane that forms angle $\theta$ with respect to the Z-axis, and includes axis X' that lies in the X-Y plane and forms angle $\phi$ with the X-axis.

A specific example of a temperature-compensated, singly rotated resonator frequently used in sensor circuits is an AT-cut quartz resonator where angle $\theta$ substantially equals 35° 15' (and angle $\phi$ equals 0°). In this regard, Martin et al., Hammond et al. and Zhang et al., cited above, describe sensors that comprise AT-cut quartz resonators.

Doubly rotated resonators are also well known in the art. A specific example of a temperature-compensated, doubly rotated resonator is an FC-cut quartz resonator wherein angle $\theta$ is about 34.5° and angle $\phi$ is about 15°. Another example of a temperature-compensated, doubly rotated resonator is an RT-cut quartz resonator wherein angle $\theta$ equals about 34.5° and angle $\phi$ is about 15°. U.S. Pat. No. 2,212,139 entitled PIEZOELECTRIC QUARTZ ELEMENT, which issued on Aug. 20, 1940 to C. F. Baldwin, et al., discloses a multiplicity of doubly rotated quartz resonators. Also, U.S. Pat. No. 2,743,144 entitled ZERO TEMPERATURE COEFFICIENT PIEZOELECTRIC CRYSTAL, which issued on Apr. 24, 1956 to V. E. Bottom, et al., discloses a crystal with a doubly rotated cut, called an IT-cut, for which angle $\theta$ is about 34° 17' and angle $\phi$ is about 19.6°. Other resonator materials and/or cutting configurations will be apparent to those skilled in these arts.

Figure 4:
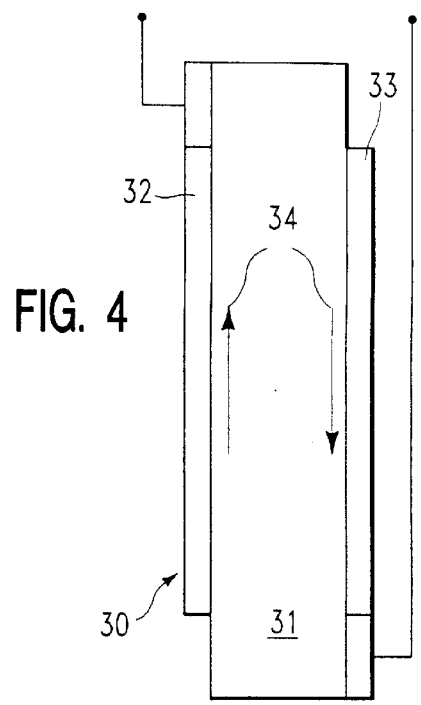
FIGS. 4 and 5 are side elevations, showing an edge of a singly rotated resonator.
Figure 5:
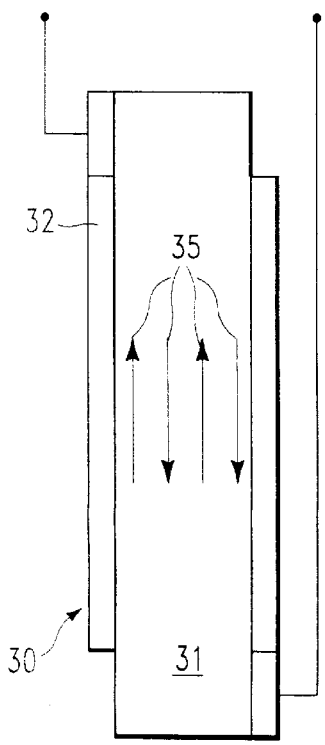

FIGS. 4 and 5 show an edge of singly rotated resonator 30 having piezoelectric plate 31 sliced from a bulk crystal (not shown) along plane 28 (see FIG. 3). Illustratively, resonator 30 may represent a standard circular, AT-cut quartz resonator. Metallic electrodes 32 and 33 are deposited on opposite major surfaces of plate 31. Arrows 34 in FIG. 4 depict the directions of mechanical vibration, at a single instant of time, that plate 31 performs in response to the application of a drive voltage across electrodes 32 and 33. In particular, arrows 34 represent operation at a fundamental, thickness-shear mode (TSM), that is, a fundamental c-mode. Resonator 30 may also be driven at other modes. For example, arrows 35 in FIG. 5 illustrate the vibration directions for resonator 30 when driven at a third-overtone c-mode. As indicated with arrows 34 and 35 in FIGS. 4 and 5, the vibrations at the major surfaces of resonator 30 are directed parallel to the planar, major surfaces of resonator 30.

Resonator 30 may be driven at other standard modes, such as a second shear mode, called the b-mode. In a b-mode, displacements of the major surfaces of a resonator are primarily in the plane of the major surfaces, as in the c-mode, but these displacements are directed perpendicular to those in a c-mode, i.e., they are directed perpendicular to arrows 34 and 35 in FIGS. 4 and 5. Another possible mode of vibration is a longitudinal mode, called the a-mode. In the a-mode, displacements at the major surfaces of a resonator are directed primarily perpendicular to the plane of the major surfaces.

As indicated above, the c-mode of a singly rotated, temperature-compensated crystal, such as an AT-cut crystal, is a pure TSM, which is characterized by surface displacements in the plane of the plate only. The modal displacements of doubly rotated crystals, on the other hand, have components that are out of the plane of the crystal plate. When a doubly rotated resonator, e.g., when $\theta \approx 35°$, and $0° \leq \phi \leq 30°$, is operated in a liquid, the displacements at the surface are not entirely in the plane of the plate. On a temperature-compensated locus of cuts, for example, as angle $\phi$ increases, the out-of-plane displacements of the c-modes of vibration also increase. The out-of-plane displacements of the b-mode and a-mode of vibration also change with angle $\phi$.

Figure 6:
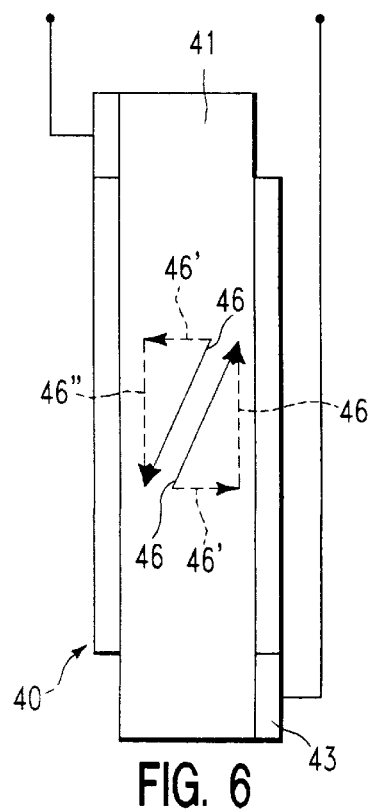
FIGS. 6 and 7 are side elevations, similar to FIGS. 4 and 5, respectively, showing an edge of a doubly rotated resonator.
Figure 7:
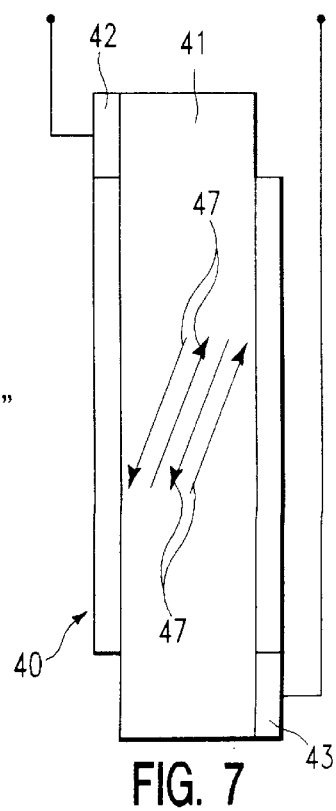

More particularly, FIGS. 6 and 7 show an edge of doubly rotated resonator 40 having piezoelectric plate 41 sliced from a bulk crystal (not shown) along plane 29 (see FIG. 3). Illustratively, resonator 40 may represent a standard circular, IT-cut, FC-cut or RT-cut quartz resonator. Metallic electrodes 42 and 43 are deposited on opposite faces of plate 41. Oblique arrows 46 in FIG. 6 depict the directions of mechanical vibration that plate 41 exhibits in response to the application of an appropriate drive voltage across electrodes 42 and 43. Arrows 46 represent oblique displacements that are directed at an angle with respect to the major surfaces of plate 41.

Arrows 46 represent the displacements obtained when resonator 40 is excited on a slow, quasi-shear mode, commonly referred to as the c-mode. Drive voltages may simultaneously excite resonator 40 on a fast, quasi-shear mode, called the b-mode, and/or on a quasi-longitudinal mode, called the a-mode. Moreover, doubly rotated resonator 40 can also be excited on various overtones, e.g., on the fundamental, third overtone and fifth overtone. Arrows 47 in FIG. 7 illustrate displacements for a third-overtone c-mode of doubly rotated resonator 40. As indicated with arrows 47 in FIG. 7, the vibrations at the third overtone also occur at an angle to the major surfaces of plate 41. All told, when considering the three different modes (a-, b-, and c-modes) and the different overtones (fundamental, third and fifth), in principle, fabricators can build resonators that may be excited at one or more of nine different frequencies. While seventh and higher overtones can also be excited, these modes exhibit high impedance, making oscillator circuit design more difficult. In addition, since the high overtones rarely provide offsetting benefits, they are rarely used.

The oblique displacements represented by arrows 46 and 47 are resolvable into in-plane and out-of-plane components. For instance, FIG. 6 shows arrow 46 resolved into in-plane component 46" and out-of-plane component 46'. Arrows 47 may be resolved into similar components. The displacements associated with out-of-plane component 46' propagate a damped compressional wave into an adjacent liquid. The displacements of in-plane component 46" propagate a damped shear wave in the liquid. Additionally, with changing values of angle $\phi$, out-of-plane components 46' of the various modes change, and so do the effects of the liquid on the frequencies (and Q's) of the various modes of vibration. Thus, resonator designers can precisely control the interaction at a resonator-fluid interface by varying angle $\phi$. Moreover, because these different modes of vibration at the different $\phi$ angles generally react differently with a fluid, each mode of vibration and $\phi$ angle will result in a different frequency change. As such, by measuring the various frequency changes, one can deduce a liquid's properties without the necessity of measuring the Q change, as in the prior art.

The operation of sensor system 11 (see FIG. 1) will now be described. Resonator 12 is first placed in air, or in another environment of known fluid properties. At least one dual-mode oscillator 13 drives resonator 12 at at least two frequencies $f_1$ and $f_2$ such that independent modes of oscillation are excited therein. For example, resonator 12 may be a doubly rotated resonator, similar to resonator 40 (see FIGS. 6 and 7), and frequencies $f_1$ and $f_2$ may be such that a fundamental c-mode and a fundamental b-mode are simultaneously excited in resonator 12, as depicted in FIGS. 6 and 7, respectively. Computer 23 monitors the outputs of counters 20 and 21 to record the output frequencies, say frequencies $f_{1A}$ and $f_{2A}$.

Resonator 12 is then immersed in non-conductive liquid 25, the properties of which are to be measured. Dual-mode oscillator 13 again drives resonator 12 while computer 23 records the outputs of frequency counters 20 and 21. Since liquid 25 mechanically loads resonator 12, it will operate at lower frequencies, say frequencies $f_{1L}$ and $f_{2L}$. The difference frequencies $\Delta f_1=(f_{1A}-f_{1L})$ and $\Delta f_2=(f_{2A}-f_{2L})$ will be related to the properties of liquid 25, such as liquid density and viscosity.

Using difference frequencies $\Delta f_1$ and $\Delta f_2$, and an appropriate set of pre-stored data that specify a functional correspondence between specific difference frequency values and known liquid properties, computer 23 produces values for the desired set of properties of liquid 25. The pre-stored data may be in the form of a look-up table or a well-known set of analytical expressions. For instance, sensor system 11 may generate an appropriate look-up table by using different reference liquids of known properties, e.g., liquids having known density, temperature and/or viscosity values, in place of liquid 25. Oscillator 13 would operate resonator 12 while it is immersed in the various reference liquids. Computer 23 would record the results, i.e., a set of reference frequencies, say frequencies $f_{1R}$ and $f_{2R}$, corresponding reference frequency differences $\Delta f_1=(f_{1A}-f_{1R})$ and $\Delta f_2=(f_{2A}-f_{2R})$, and the corresponding known liquid property values for the reference liquids.

Alternatively, well-known analytic functions, which model resonators and relate frequency differences $[\Delta f_1, \Delta f_2]$ with known property values, such as liquid density, viscosity and temperature values, may be stored in computer 23. Thus, as an alternative, computer 23 may compute the unknown properties of a liquid using these analytical expressions and a set of measured frequency differences $[\Delta f_1, \Delta f_2]$.

It is contemplated that the technique depicted in FIG. 1 may be extended to one in which three or more modes of resonator 12 are operated simultaneously while in liquid 25. In particular, oscillators may drive resonator 12 simultaneously with frequencies $f_3$, $f_4$ and $f_5$ to excite a fundamental c-mode, a fundamental b-mode and a third-overtone c-mode. Using corresponding frequency differences $\Delta f_3$, $\Delta f_4$ and $\Delta f_5$, due to immersion of resonator 12 in fluid 25, computer 23 may simultaneously determine three fluid properties, such as the viscosity, density and temperature of liquid 25.

Figure 8:
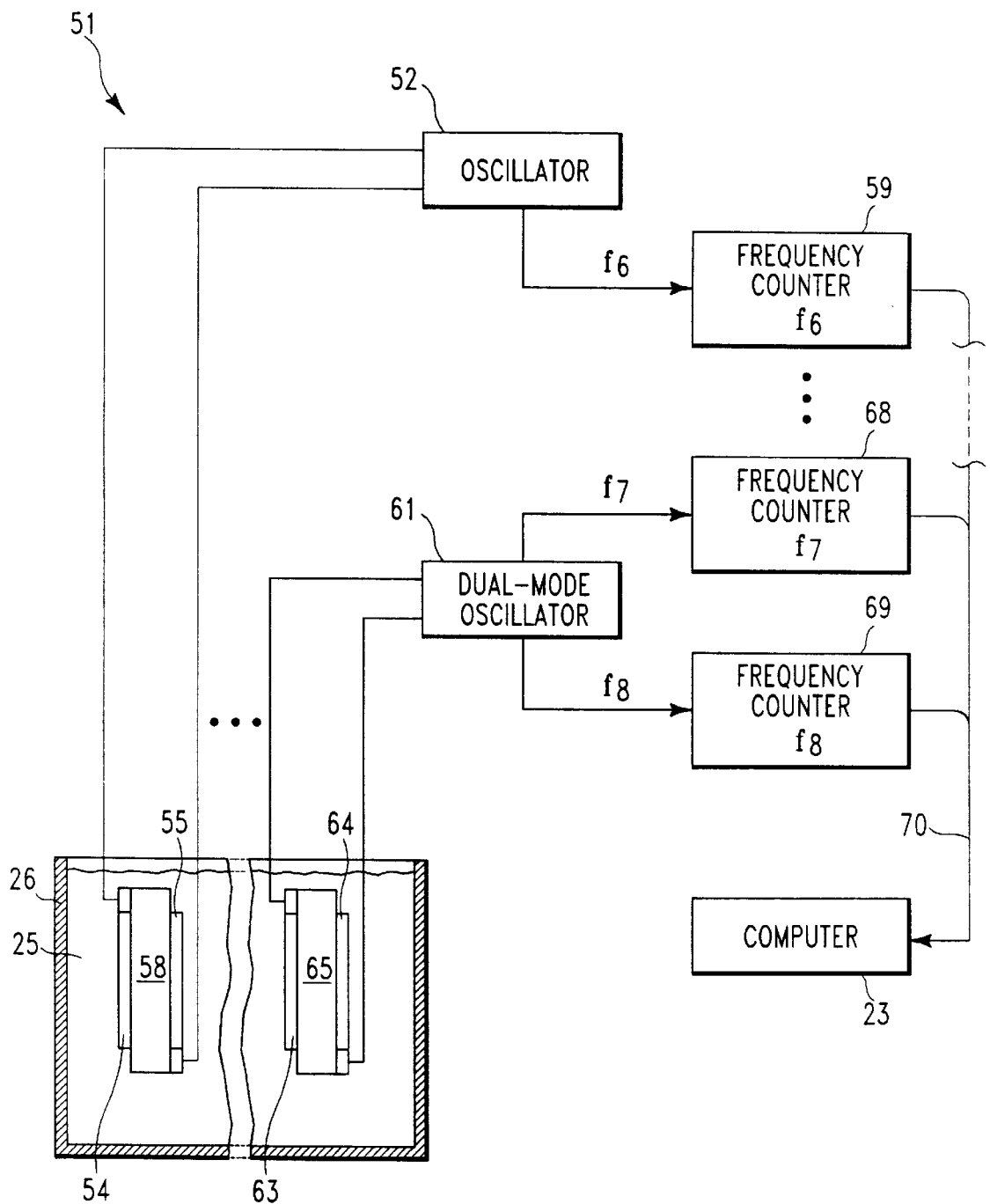
FIG. 8 is a schematic diagram, similar to FIG. 1, of a modified sensor system with a plurality of piezoelectric resonators immersed in a liquid in accordance with the present invention.

It is further contemplated that the technique depicted in FIG. 1, may be extended to one in which multiple resonators, each of a different angle $\phi$, are operated simultaneously in liquid 25, as illustrated in FIG. 8. In particular, sensor system 51 comprises oscillator 52 connected to electrodes 54 and 55 for driving resonator 58 at a single frequency $f_6$. Oscillator 52 has an $f_6$ output connected to frequency counter 59. Dual-mode oscillator 61 connects to electrodes 63 and 64 to drive resonator 65 at frequencies $f_7$ and $f_8$. Resonators 58 and 65 are placed in liquid 25.

Oscillator 61 has $f_7$ and $f_8$ outputs connected to frequency counters 68 and 69, respectively. The outputs of counters 59, 68 and 69 communicate with computer 23 via bus 70. While FIG. 8 depicts two oscillators for driving resonators 58 and 65 at three frequencies, $f_6$, $f_7$ and $f_8$, sensor system 51 may have additional resonators of different angles phi being driven at still additional frequencies, as indicated by the dashed lines in FIG. 8. As mentioned above, these additional frequencies will render sensor system 51 capable of determining a greater number of fluid properties.

As a specific example, resonator 58 of FIG. 8 may be an AT-cut quartz resonator driven in a fundamental c-mode (see resonator 30 in FIG. 4). Also, resonator 65 may be a doubly rotated cut resonator, e.g., angle $\phi=4°$, driven at fundamental and third-overtone c-mode frequencies (see resonator 40 in FIGS. 6 and 7). As such, oscillator 52 drives resonator 58 at frequency $f_6$ while dual-mode oscillator 61 drives resonator 65 at frequencies $f_7$ and $f_8$. Counters 59, 68 and 69 transmit frequency data to computer 23. In response, computer 23 calculates the frequency differences $\Delta f_6=(f_{6A}-f_{6L})$, $\Delta f_7=(f_{7A}-f_{7L})$ and $\Delta f_8=(f_{8A}-f_{8L})$; where $f_{6A}$, $f_{7A}$ and $f_{8A}$ correspond to frequency measurements made with resonators 58 and 65 operated in air, and $f_{6L}$, $f_{7L}$ and $f_{8L}$ represent corresponding frequency measurements made with resonators 58 and 65 operated in liquid 25. Computer 23 uses these independent frequency differences $\Delta f_6$, $\Delta f_7$ and $\Delta f_8$, and an appropriate look-up table or an analytical model to determine the values of three liquid properties, such as liquid density, viscosity and temperature.

The above description depicts liquid 25 as being non-conductive. However, sensor systems 11 and 51 may also be used to measure the properties of conductive liquids. When both major surfaces of resonators 12, 58 and 65 are fully immersed, liquid 25 must be non-conductive to prevent short circuiting their electrodes. Those skilled in the art, however, will appreciate that the present technique may be used with conductive liquids by contacting only a portion, say only one major surface, of resonators 12, 58 and 65 with liquid 25.

Methods of placing a resonator in contact with a fluid can include the following: 1) complete immersion of all surfaces of the resonator, as depicted in FIGS. 1 and 8; 2) partial immersion of both major surfaces of the resonator; and 3) placing only one major side of the resonator in contact with the fluid. A partial-immersion method can be especially useful for resonators with angles of cut that produce large out-of-plane components of the displacement (see out-of-plane components 46' in FIG. 6). Due to the damping caused by a fluid, the frequencies of those resonators are often difficult to measure when they are fully immersed in the fluid. However, if the resonator is immersed at a controlled rate and, therefore, the damping increased gradually, computer 23 may use measurements of frequency changes versus immersion depth to determine the properties of fluid 25.

In this regard, the ratios of in-plane displacements to out-of-plane displacements for particular crystal cuts and vibration modes can vary widely. The following table lists analytically derived ratio values for quartz crystals:

TABLE A

| Name of cut | θ (in degrees) | φ (in degrees) | Ratio of in-plane to out-of-plane displacements | | |
|---|---|---|---|---|---|
| | | | a-mode | b-mode | c-mode |
| AT-cut | 35.25 | 0 | 0.06 | 16.0 | ∞ |
| 3° V-cut | 35.07 | 3.0 | 0.07 | 15.5 | 30.4 |
| 5° V-cut | 34.94 | 5.0 | 0.09 | 15.1 | 18.2 |
| 10° V-cut | 34.6 | 10 | 0.13 | 14.2 | 9.1 |
| FC-cut | 34.3 | 15 | 0.18 | 13.4 | 6.1 |
| IT-cut | 34.1 | 19.1 | 0.22 | 13.2 | 4.8 |
| SC-cut | 33.9 | 21.9 | 0.26 | 13.6 | 4.1 |
| 25° V-cut | 33.7 | 25 | 0.29 | 14.9 | 3.6 |
| 30° V-cut | 33.4 | 30 | 0.34 | 25.5 | 3.0 |
| 42.5° V-cut | 35.8 | 42.5 | 0.42 | 4.9 | 2.9 |
| BT-cut | −49.2 | 0 | 0.21 | ∞ | 4.7 |

Another important parameter in selecting proper values for angles θ and φ for a particular sensing application is the coupling factor. Not all displacements can be realized with conventional resonators. For example, an AT-cut's a-mode and b-mode cannot be excited because the coupling to these modes is zero. However, since the coupling to the c-mode is 8.8%, the c-mode can be readily excited. At φ angles greater than zero degrees, all three modes can be excited. For example, when the φ angle is equal to about five degrees, the coupling to the a-mode is 0.8%, the coupling to the b-mode is 1.3%, and the coupling to the c-mode is 8.6%.

While the present invention represents a substantial improvement of standard fluid measuring and testing techniques, important new applications of the present techniques will also appear to those skilled in these arts. For instance, due to the inaccuracies of Q measurements, prior liquid sensors typically measure relatively large changes in the properties of fluids, such as crankcase oil (see the Hammond et al. article cited above). However, because of the increased accuracy and sensitivity of the present techniques, sensors made in accordance with the present invention have important new applications, for instance, as monitors of minute irregularities in body fluids.

Other modes of vibration are also possible. Thus, when resonator 12 operates in liquid 19, as shown in FIG. 1, c-mode thickness shear vibrations at its surface entrain adjacent liquid layers, which results in the generation of a non-propagating, viscously coupled shear wave in liquid 25. The shear-wave penetration depth (δ) of a liquid is a measure of the ability of a liquid to support a shear wave. Specifically, shear-wave penetration depth (δ) is related to a liquid's properties according to the following expression: $\delta = (\eta/\pi f \rho)$, where (η) is the viscosity and (ρ) is the density of the liquid, and f is the shear-wave frequency. Curve 60 in FIG. 9 graphically depicts shear-wave penetration depth (δ) for a typical liquid. Curve 60 plots magnitude (M) of a shear wave as a function of a distance (D) measured from the shear wave source, i.e., from the face of the resonator generating the shear wave. Curve 60 shows a monotonic decrease in magnitude (M) with increasing distance (D). Shear-wave penetration depth (δ) for curve 60 corresponds to that distance (D) at which the magnitude (M) is reduced to (1/e), or approximately 36.8%, of the value at the resonator surface (i.e., the maximum value depicted by point 61 in FIG. 9). For example, sensor system 11 may measure shear-wave penetration depth (δ) by moving resonator 12 into close proximity with side wall 26. These movements are such that gap width (g) ranges between zero (where resonator 12 would touch wall 26) and one-half wavelength i.e., $0 < g < (\lambda/2)$. Within this close range, wall 26 encounters shear waves generated by resonator 12 (see FIG. 9 and in-plane components 46" in FIG. 6).

Figure 9:
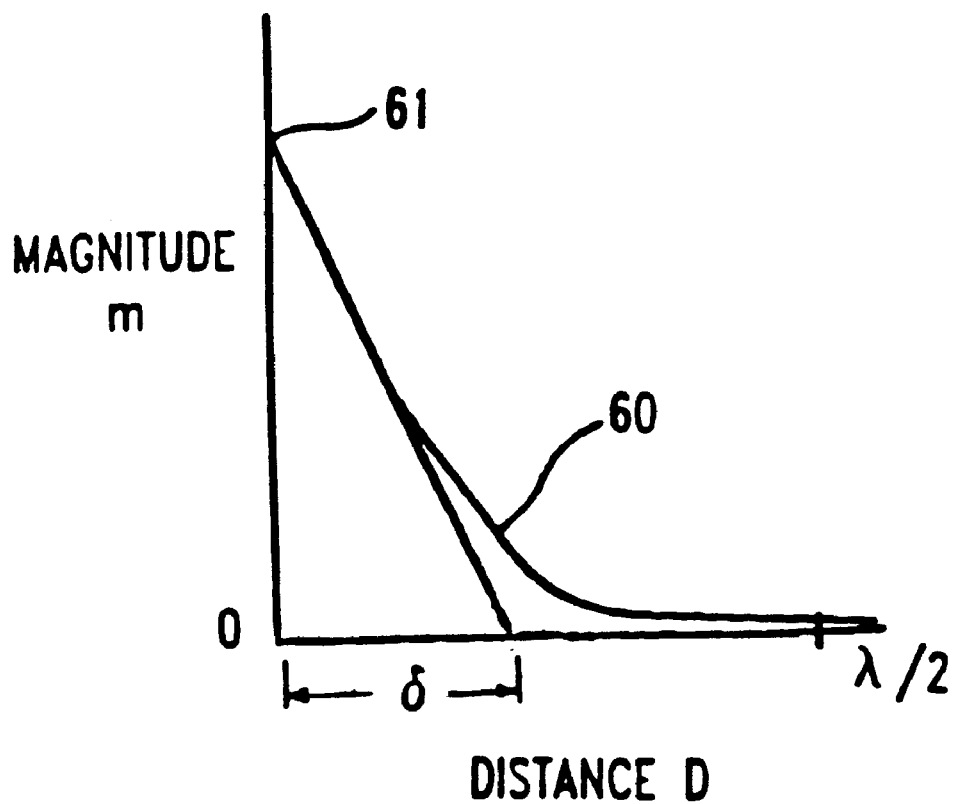
FIG. 9 is a graph of shear-wave magnitude (M) versus distance (D) useful in understanding the property of shear-wave penetration depth ($\delta$) of a liquid with an acoustic wavelength $\lambda$.

Coupling between these shear waves and wall 26 represents still an additional mechanical load on resonator 12, which increases as gap width (g) approaches zero (see distance D in FIG. 9). The shear-wave loading of resonator 12 manifests itself in corresponding variations in the frequency response of resonator 12. As such, frequency deviations at the output of frequency counter 20 will generally vary in a manner similar to the variations of shear-wave magnitude M in curve 60 of FIG. 9. After storing a set of appropriate frequency changes, computer 23 determines shear-wave penetration depth (δ) by calculating, e.g., the gap width (g) at which the frequency deviation is reduced to (1/e), or about 36.8% of its maximum value (attained for gap widths (g) approaching zero).

Obviously many other applications, modifications and variations of the present invention are possible in the light of the above teachings. While FIGS. 1 and 2 show only a schematic illustration of resonator 12, those skilled in these arts will recognize that, in practice, resonator 12 may be mounted in any one of a variety of package mountings suitable for use in different fluid sensing applications. Further, the present techniques do not require resonators with rough or textured surfaces, but resonators 12, 58 and 65 may have one or more of their surfaces textured. However, since it is usually easier to fabricate systems 11 and 51 with resonators having only easily reproducible polished surfaces, that technique is preferred.

The invention may also be applied to composite resonators, for example, zinc oxide as the piezoelectric layer on top of silicon, and to resonators made of materials other than quartz; for example, the langasite family of materials, and lithium tetraborate materials. In general, resonator materials are categorized, for the properties pertinent to the present invention, by the crystallographic point group. Thus, quartz and members of the langasite family belong to point group 3 m. Other applicable materials and their point groups include: lithium tetraborate (4 mm); certain binary piezoelectric semiconductors, such as gallium nitride, aluminum nitride, and α-silicon carbide belonging to the wurtzite structure (6 mm); electroceramics, such as poled barium titanate and lead zirconate alloys (6 mm); and binary and ternary piezoelectric semiconductors of the zincblende structure, such as gallium arsenide and β-silicon carbide (4-bar 3 m). Plate resonators fabricated from any crystalline material will exhibit the presence of three thickness modes (the a-, b-, and c-modes previously described), and their overtones. Depending on the point group of the crystal, a singly rotated cut may have a c-mode that has its displacement in the plane of the plate; this is the case with quartz, and all materials with point symmetry 32. With materials of other symmetries, the situation may be different, but, mutatis mutandis, the teachings given herein may be applied to produce resonators whose modal frequencies are differently affected by liquid loading, and, when used in concert in the manner described herein, can be used to uniquely determine the properties of a liquid measurand.

The excitation mechanism need not be piezoelectric. Any resonator capable of being stimulated into resonant or non-resonant mechanical motion may be used. The means of excitation may be piezoelectricity, electrostriction, biased electrostriction (which behaves like piezoelectricity, but the coefficient can be adjusted by a dc bias), piezomagnetism, magnetostriction, biased magnetostriction, or other driving mechanism, singly, or in combination.

Q change measurements may also be used in the present invention in combination with the multiple frequency change measurements. Thus, many applications and variations of the present invention will become evident to those skilled in these arts in the light of the above teachings. It is to be understood, therefore, that within the scope of the appended claims, the invention may be practiced otherwise than as specifically described.

What is claimed is:

1. A sensor for determining the properties of a liquid comprising:
    a resonator means having at least one liquid-contacting surface;
    an oscillator means connected to said resonator means for driving said resonator means simultaneously at a plurality of different frequencies;
    a frequency means connected to said oscillator means for measuring the operating frequencies of said resonator means when said surfaces are in contact with said liquid;
    said properties of the liquid include density and viscosity; and
    a liquid property means responsive to said frequency means for determining difference frequencies by comparing said operating frequencies measured by said frequency means with predetermined reference frequencies, and for determining said properties of said liquid from said difference frequencies without measuring quality factor, Q.

2. The sensor of claim 1 wherein said resonator means comprises at least one resonator and said oscillator means drives said at least one resonator at at least two different frequencies.

3. The sensor of claim 2 wherein said at least one resonator comprises a singly rotated piezoelectric resonator.

4. The sensor of claim 2 wherein said at least one resonator is a doubly rotated piezoelectric resonator.

5. The sensor of claim 4 wherein said oscillator means drives said doubly rotated resonator simultaneously in at least a fundamental c-mode and a third overtone c-mode.

6. The sensor of claim 4 wherein said oscillator means drives said doubly rotated resonator simultaneously in a fundamental c-mode and a fundamental b-mode.

7. The sensor of claim 1 wherein said resonator means includes a doubly rotated quartz resonator and said liquid-contacting surface includes a polished surface.

8. The sensor of claim 7 further comprising a liquid means for immersing at least a portion of said doubly rotated quartz resonator in said liquid and wherein said reference frequencies correspond to air-operating frequencies of said resonator.

9. The sensor of claim 8 wherein said oscillator means drives said doubly rotated quartz resonator simultaneously in at least a fundamental c-mode and a third overtone c-mode.

10. The sensor of claim 8 further comprising:
    said oscillator means drives said doubly rotated quartz resonator simultaneously in a fundamental c-mode and a fundamental b-mode;
    said doubly rotated quartz resonator causing a plurality of oblique displacements including a plurality of out-of-plane components;
    said out-of-plane components propagating a damped compressional wave into said the liquid adjacent to said resonator;
    said out-of-plane components being effected by a variation of angle $\phi$; and
    said variations of angle $\phi$ allowing precise control of a resonator-fluid interface and a different frequency change permitting accurate measurement of said liquid properties independent of measuring Q changes.

11. The sensor of claim 10, further comprising said plurality of oblique displacements including a plurality of in-plane components that propagate a damped shear wave into said liquid.

12. The sensor of claim 8, further comprising said liquid property means being connected to a data processing means.

13. The sensor of claim 12, further comprising:
    said data processing means storing a plurality of resonator analytic expressions;
    said data processing means storing a plurality of frequency differences; and
    said data processing means storing a plurality of known liquid property values.

14. The sensor of claim 13, further comprising said data processing means calculating said difference frequencies.

15. The sensor of claim 14, further comprising said data processing means calculating a plurality of unknown properties of the liquid using said plurality of resonator analytical expressions and a set of measured frequency differences.

16. The sensor of claim 1, further comprising operating at least three modes of said resonator means simultaneously while in said liquid.

17. The sensor of claim 16, further comprising said oscillator means driving said resonator means simultaneously with three frequencies to excite a fundamental c-mode, a fundamental b-mode and a third-overtone c-mode.

18. The sensor of claim 17, further comprising:
    employing a plurality of corresponding frequency differences; and
    said data processing means determines a plurality of said properties of the liquid in real time.

19. The sensor of claim 18, further comprising said liquid being non-conductive.

20. The sensor of claim 19, further comprising said resonator means being fully immersed in said liquid.

21. The sensor of claim 18, further comprising said liquid being conductive.

22. A sensor for determining the properties of a liquid comprising:
    a plurality of piezoelectric resonators, each of said resonators having a liquid-contacting surface;
    an oscillator means connected to said plurality of resonators for driving each of said resonators, and for driving at least one of said resonators simultaneously at a plurality of different frequencies;
    a frequency means connected to said oscillator means for measuring the operating frequencies of said resonators when said surfaces are in contact with said liquid;
    the properties of said liquids include density and viscosity; and
    a liquid property means responsive to said frequency means for determining difference frequencies by comparing said operating frequencies measured by said frequency means with predetermined reference frequencies, and for determining said properties of said liquid from said difference frequencies without measuring quality factor Q.

23. The sensor of claim 22 wherein at least one of said resonators comprises a singly rotated resonator.

24. The sensor of claim 23 wherein said singly rotated resonator comprises an AT-cut quartz resonator.

25. The sensor of claim 22 wherein at least one of said resonators comprises a doubly rotated resonator.

26. The sensor of claim 25 wherein said oscillator means drives said doubly rotated resonator simultaneously in at least a fundamental c-mode and a third overtone c-mode.

27. The sensor of claim 25 wherein said oscillator means drives said doubly rotated resonator simultaneously in a fundamental c-mode and a fundamental b-mode.

28. The sensor of claim 25 further comprising a liquid means for immersing at least a portion of said doubly rotated resonator in said liquid, and wherein said reference frequencies correspond to air-operating frequencies of said resonators and said liquid-contacting surfaces are polished surfaces.

29. The sensor of claim 25, further comprising a liquid means for immersing said doubly rotated resonator in said liquid.

30. The sensor of claim 25, further comprising said liquid means allows placing a major side of said doubly rotated resonator in said liquid.

31. The sensor of claim 22, further comprising said liquid property means being connected to a data processing means.

32. The sensor of claim 31, further comprising each of said plurality of resonators, having a different angle $\phi$, being operated simultaneously in said liquid.

33. The sensor of claim 32, further comprising:
said oscillator means is connected to a first pair of electrodes to drive a first one of said plurality of resonators at a first frequency, said oscillator mean provides a first output to said frequency means;
a dual-mode oscillator being connected to said frequency means and to a second pair of electrodes to drive a second one of the plurality of resonators at a second frequency and at a third frequency;
said dual-mode oscillator provides a second output and a third output to said frequency means; and
said first output, said second output and said third output are communicated to said date processing means.

34. The sensor of claim 33, further comprising said first resonator is an AT-cut quartz resonator driven in a fundamental c-mode.

35. The sensor of claim 34, further comprising said second resonator is a doubly rotated cut resonator is driven at fundamental and third-overtone c-mode frequencies.

36. The sensor of claim 35, further comprising said doubly rotated cut resonator having an angle $\phi=4°$.

37. The sensor of claim 36, further comprising said data processing means calculating said difference frequencies.

38. A method of determining the properties of a liquid comprising the steps of:
providing a resonator means with a fluid-contacting surface;
exposing said fluid-contacting surface to a reference fluid having known properties;
driving said resonator means simultaneously at a plurality of different frequencies;
measuring the fluid-operating frequencies of said resonator means while said surface is in contact with said reference fluid;
exposing said fluid-contacting surface to said liquid;
driving said resonator means simultaneously at said plurality of different frequencies;
measuring the liquid-operating frequencies of said resonator means while said surface is in contact with said liquid, the properties of said liquid include density and viscosity;
determining difference frequencies by comparing said fluid-operating frequencies with said liquid-operating frequencies; and
determining said properties of said liquid from said difference frequencies without measuring quality factor, Q.

39. The method of claim 38 wherein said providing step further comprises providing at least one singly rotated piezoelectric resonator.

40. The method of claim 39 wherein said providing step further comprises providing an AT-cut quartz resonator.

41. The method of claim 38 wherein said providing step further comprises providing at least one doubly rotated piezoelectric resonator.

42. The method of claim 41 wherein said driving steps each further comprises driving said doubly rotated resonator simultaneously in at least a fundamental c-mode and a third overtone c-mode.

43. The method of claim 41 wherein said driving step comprises driving said doubly rotated resonator simultaneously in a fundamental c-mode and a fundamental b-mode.

44. The method of claim 41 wherein said step of exposing said fluid-contacting surface to said liquid includes immersing at least a portion of said doubly rotated resonator in said liquid.

45. A method of determining the properties of a liquid comprising:
providing a plurality of piezoelectric resonators each with a fluid-contacting surface;
exposing said fluid-contacting surfaces to a reference fluid having known properties;
driving said resonators and driving at least one of said resonators simultaneously at a plurality of different frequencies;
measuring the fluid-operating frequencies of said resonators while said surfaces are in contact with said reference fluid;
exposing said fluid-contacting surfaces to said liquid;
driving said resonators and driving said at least one of said resonators simultaneously at said plurality of different frequencies;
measuring the liquid-operating frequencies of said resonators while said surfaces are in contact with said liquid, the properties of said liquid include density and viscosity;
determining difference frequencies by comparing said fluid-operating frequencies with corresponding ones of said liquid-operating frequencies; and
determining said properties of said liquid from said difference frequencies without measuring quality factor, Q.

46. The method of claim 45 wherein said providing step includes providing at least one singly rotated resonator and one doubly rotated resonator, and said driving steps include driving said doubly rotated resonator simultaneously in at least a fundamental c-mode and a third overtone c-mode.

47. The method of claim 45 wherein said providing step includes providing at least one singly rotated resonator and one doubly rotated resonator, and said driving steps include driving said doubly rotated resonator simultaneously in at least a fundamental c-mode and a fundamental b-mode.

* * * * *